United States Patent
Seo et al.

(10) Patent No.: US 12,076,393 B2
(45) Date of Patent: Sep. 3, 2024

(54) VACCINE COMPOSITION FOR PREVENTION OR TREATMENT OF SARS-CORONAVIRUS-2 INFECTION

(71) Applicant: SK BIOSCIENCE CO., LTD., Gyeonggi-do (KR)

(72) Inventors: Ki-weon Seo, Gyeonggi-do (KR); Teawoo Kwon, Gyeonggi-do (KR); Eun-som Kim, Gyeonggi-do (KR); Chi-Yong Kim, Gyeonggi-do (KR); Yoonjae Lee, Gyeonggi-do (KR); Seung-hye Hong, Gyeonggi-do (KR)

(73) Assignee: SK BIOSCIENCE CO., LTD., Gyeonggi-do (KR)

( * ) Notice: Subject to any disclaimer, the term of this patent is extended or adjusted under 35 U.S.C. 154(b) by 0 days.

(21) Appl. No.: 18/034,141

(22) PCT Filed: Oct. 27, 2021

(86) PCT No.: PCT/KR2021/015262
§ 371 (c)(1),
(2) Date: Aug. 30, 2023

(87) PCT Pub. No.: WO2022/092828
PCT Pub. Date: May 5, 2022

(65) Prior Publication Data
US 2024/0042008 A1    Feb. 8, 2024

(30) Foreign Application Priority Data
Oct. 28, 2020    (KR) .................. 10-2020-0141598

(51) Int. Cl.
| | | |
|---|---|---|
| A61K 39/215 | (2006.01) | |
| A61P 31/14 | (2006.01) | |
| C07K 14/165 | (2006.01) | |
| C12N 1/20 | (2006.01) | |
| C12N 15/70 | (2006.01) | |
| A61K 39/00 | (2006.01) | |

(52) U.S. Cl.
CPC .......... *A61K 39/215* (2013.01); *A61P 31/14* (2018.01); *C07K 14/165* (2013.01); *C12N 1/205* (2021.05); *C12N 15/70* (2013.01); *A61K 2039/55505* (2013.01)

(58) Field of Classification Search
None
See application file for complete search history.

(56) References Cited

U.S. PATENT DOCUMENTS
2018/0334480 A1    11/2018    Gershoni

FOREIGN PATENT DOCUMENTS

| CN | 111440229 A | 7/2020 |
|---|---|---|
| CN | 111662389 A | 9/2020 |
| CN | 111217917 B | 10/2020 |
| WO | WO-2021/221486 A1 | 11/2021 |
| WO | WO-2022/042542 A1 | 3/2022 |

OTHER PUBLICATIONS

Hong et al., Sci. Adv. 2021; 7:eabg7156, 10 pages (Year: 2021).*
International Search Report from corresponding PCT Application No. PCT/KR2021/015262, dated Mar. 14, 2022.
Yarmarkovich, M., et al.; "Identification of SARS-CoV-2 Vaccine Epitopes Predicted to Induce Long-Term Population-Scale Immunity" 2020, Cell Reports Medicine 1, 100036, pp. 1-13.
Zeltins, A., et al.; "Incorporation of tetanus-epitope into virus-like particles achieves vaccine responses even in older recipients in models of psoriasis", Alzheimer's and cat allergy. npj Vaccines, 2017, vol. 2, article No. 30, pp. 1-13.
Yang, J., et al. : A vaccine targeting the RBD of the S protein of SARS-CoV-2 induces protective immunity, Nature, vol. 586, 2020.
Yu, J., et al.; "DNA vaccine protection against SARS-CoV-2 in rhesus macaques", Science 369, 806-811, 2020, pp. 1-6.
Wen, X., et al.; "Inclusion of a universal tetanus toxoid CD4+ T cell epitope P2 significantly enhanced the immunogenicity of recombinant rotavirus DVP8* subunit parenteral vaccines", Vaccine 32 (2014) 4420-4427.
Office Action from corresponding Korean Patent Application No. 10-2021-0145047, dated Feb. 25, 2022.
Office Action from corresponding Korean Patent Application No. 10-2021-0145047, dated Sep. 29, 2022.
Notice of Allowance from corresponding Korean Patent Application No. 10-2021-0145047. dated Feb. 21, 2023.
Rosa La C Et Al: "Preclinical development of an adjuvant-free peptide vaccine with activity against CMV pp65 in HLA transgenic mice", Blood, American Society of Hematology, US, vol. 100, No. 10, Nov. 15, 2002 (Nov. 15, 2002), pp. 3681-3689, XP002277230, ISSN: 0006-4971, DOI: 10.1182/BLOOD-2002-03-092.
Qi Xiaoxiao Et Al: "Construction and immunogenic studies of a mFc fusion receptor binding domain (RBD) of spike protein as a subunit vaccine agaiinst SARS-CoV-2 infection", Chemical Communications,vol. 56, No. 61, Jul. 31, 2020 (Jul. 31, 2020), pp. 8683-8686, XP055876579, UK ISSN: 1359-7345, DOI: 10.1039/DOCC03263H.
European Search Report from corresponding European Application No. 21886822.2, dated Jun. 13, 2024.

* cited by examiner

*Primary Examiner* — Stacy B Chen
(74) *Attorney, Agent, or Firm* — Harness, Dickey & Pierce, P.L.C.

(57) ABSTRACT

The present invention provides a recombinant antigen protein for preventing SARS-coronavirus-2 infection, comprising a polypeptide derived from an S1 subunit of a spike protein of SARS-coronavirus-2 and a polypeptide constituting a tetanus toxin (TT) epitope P2 domain, and a vaccine composition comprising the same.

15 Claims, 2 Drawing Sheets
Specification includes a Sequence Listing.

SEQUENCE LISTING

```
<160> NUMBER OF SEQ ID NOS: 28

<210> SEQ ID NO 1
<211> LENGTH: 15
<212> TYPE: PRT
<213> ORGANISM: Artificial Sequence
<220> FEATURE:
<223> OTHER INFORMATION: Tetanus toxoid P2 epitope  peptide

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 673
<212> TYPE: PRT
<213> ORGANISM: Artificial Sequence
<220> FEATURE:
<223> OTHER INFORMATION: the fragment from 14 to 686 amino acids of S
      protein of Sars-cov-2

<400> SEQUENCE: 2

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205
```

```
Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
            450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
610                 615                 620
```

-continued

```
Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670

Ser

<210> SEQ ID NO 3
<211> LENGTH: 269
<212> TYPE: PRT
<213> ORGANISM: Artificial Sequence
<220> FEATURE:
<223> OTHER INFORMATION: the fragment from 323 to 591 amino acids of S
      protein of Sars-cov-2

<400> SEQUENCE: 3

Thr Glu Ser Ile Val Arg Phe Pro Asn Ile Thr Asn Leu Cys Pro Phe
1               5                   10                  15

Gly Glu Val Phe Asn Ala Thr Arg Phe Ala Ser Val Tyr Ala Trp Asn
            20                  25                  30

Arg Lys Arg Ile Ser Asn Cys Val Ala Asp Tyr Ser Val Leu Tyr Asn
        35                  40                  45

Ser Ala Ser Phe Ser Thr Phe Lys Cys Tyr Gly Val Ser Pro Thr Lys
    50                  55                  60

Leu Asn Asp Leu Cys Phe Thr Asn Val Tyr Ala Asp Ser Phe Val Ile
65                  70                  75                  80

Arg Gly Asp Glu Val Arg Gln Ile Ala Pro Gly Gln Thr Gly Lys Ile
                85                  90                  95

Ala Asp Tyr Asn Tyr Lys Leu Pro Asp Asp Phe Thr Gly Cys Val Ile
            100                 105                 110

Ala Trp Asn Ser Asn Asn Leu Asp Ser Lys Val Gly Gly Asn Tyr Asn
        115                 120                 125

Tyr Leu Tyr Arg Leu Phe Arg Lys Ser Asn Leu Lys Pro Phe Glu Arg
    130                 135                 140

Asp Ile Ser Thr Glu Ile Tyr Gln Ala Gly Ser Thr Pro Cys Asn Gly
145                 150                 155                 160

Val Glu Gly Phe Asn Cys Tyr Phe Pro Leu Gln Ser Tyr Gly Phe Gln
                165                 170                 175

Pro Thr Asn Gly Val Gly Tyr Gln Pro Tyr Arg Val Val Val Leu Ser
            180                 185                 190

Phe Glu Leu Leu His Ala Pro Ala Thr Val Cys Gly Pro Lys Lys Ser
        195                 200                 205

Thr Asn Leu Val Lys Asn Lys Cys Val Asn Phe Asn Phe Asn Gly Leu
    210                 215                 220

Thr Gly Thr Gly Val Leu Thr Glu Ser Asn Lys Lys Phe Leu Pro Phe
225                 230                 235                 240

Gln Gln Phe Gly Arg Asp Ile Ala Asp Thr Thr Asp Ala Val Arg Asp
                245                 250                 255

Pro Gln Thr Leu Glu Ile Leu Asp Ile Thr Pro Cys Ser
            260                 265

<210> SEQ ID NO 4
<211> LENGTH: 217
<212> TYPE: PRT
<213> ORGANISM: Artificial Sequence
<220> FEATURE:
```

<223> OTHER INFORMATION: the fragment from 321 to 537 amino acids of S
      protein of Sars-cov-2

<400> SEQUENCE: 4

Gln Pro Thr Glu Ser Ile Val Arg Phe Pro Asn Ile Thr Asn Leu Cys
1               5                   10                  15

Pro Phe Gly Glu Val Phe Asn Ala Thr Arg Phe Ala Ser Val Tyr Ala
            20                  25                  30

Trp Asn Arg Lys Arg Ile Ser Asn Cys Val Ala Asp Tyr Ser Val Leu
        35                  40                  45

Tyr Asn Ser Ala Ser Phe Ser Thr Phe Lys Cys Tyr Gly Val Ser Pro
    50                  55                  60

Thr Lys Leu Asn Asp Leu Cys Phe Thr Asn Val Tyr Ala Asp Ser Phe
65                  70                  75                  80

Val Ile Arg Gly Asp Glu Val Arg Gln Ile Ala Pro Gly Gln Thr Gly
                85                  90                  95

Lys Ile Ala Asp Tyr Asn Tyr Lys Leu Pro Asp Asp Phe Thr Gly Cys
            100                 105                 110

Val Ile Ala Trp Asn Ser Asn Asn Leu Asp Ser Lys Val Gly Gly Asn
        115                 120                 125

Tyr Asn Tyr Leu Tyr Arg Leu Phe Arg Lys Ser Asn Leu Lys Pro Phe
    130                 135                 140

Glu Arg Asp Ile Ser Thr Glu Ile Tyr Gln Ala Gly Ser Thr Pro Cys
145                 150                 155                 160

Asn Gly Val Glu Gly Phe Asn Cys Tyr Phe Pro Leu Gln Ser Tyr Gly
                165                 170                 175

Phe Gln Pro Thr Asn Gly Val Gly Tyr Gln Pro Tyr Arg Val Val Val
            180                 185                 190

Leu Ser Phe Glu Leu Leu His Ala Pro Ala Thr Val Cys Gly Pro Lys
        195                 200                 205

Lys Ser Thr Asn Leu Val Lys Asn Lys
    210                 215

<210> SEQ ID NO 5
<211> LENGTH: 181
<212> TYPE: PRT
<213> ORGANISM: Artificial Sequence
<220> FEATURE:
<223> OTHER INFORMATION: the fragment from 336 to 516 amino acids of S
      protein of Sars-cov-2

<400> SEQUENCE: 5

Cys Pro Phe Gly Glu Val Phe Asn Ala Thr Arg Phe Ala Ser Val Tyr
1               5                   10                  15

Ala Trp Asn Arg Lys Arg Ile Ser Asn Cys Val Ala Asp Tyr Ser Val
            20                  25                  30

Leu Tyr Asn Ser Ala Ser Phe Ser Thr Phe Lys Cys Tyr Gly Val Ser
        35                  40                  45

Pro Thr Lys Leu Asn Asp Leu Cys Phe Thr Asn Val Tyr Ala Asp Ser
    50                  55                  60

Phe Val Ile Arg Gly Asp Glu Val Arg Gln Ile Ala Pro Gly Gln Thr
65                  70                  75                  80

Gly Lys Ile Ala Asp Tyr Asn Tyr Lys Leu Pro Asp Asp Phe Thr Gly
                85                  90                  95

Cys Val Ile Ala Trp Asn Ser Asn Asn Leu Asp Ser Lys Val Gly Gly
            100                 105                 110

-continued

```
Asn Tyr Asn Tyr Leu Tyr Arg Leu Phe Arg Lys Ser Asn Leu Lys Pro
            115                 120                 125

Phe Glu Arg Asp Ile Ser Thr Glu Ile Tyr Gln Ala Gly Ser Thr Pro
        130                 135                 140

Cys Asn Gly Val Glu Gly Phe Asn Cys Tyr Phe Pro Leu Gln Ser Tyr
145                 150                 155                 160

Gly Phe Gln Pro Thr Asn Gly Val Gly Tyr Gln Pro Tyr Arg Val Val
                165                 170                 175

Val Leu Ser Phe Glu
            180

<210> SEQ ID NO 6
<211> LENGTH: 694
<212> TYPE: PRT
<213> ORGANISM: Artificial Sequence
<220> FEATURE:
<223> OTHER INFORMATION: SK-E-S1-P2

<400> SEQUENCE: 6

Met Gln Tyr Ile Lys Ala Asn Ser Lys Phe Ile Gly Ile Thr Glu Leu
1               5                   10                  15

Gly Ser Gly Ser Gly Gln Cys Val Asn Leu Thr Thr Arg Thr Gln Leu
            20                  25                  30

Pro Pro Ala Tyr Thr Asn Ser Phe Thr Arg Gly Val Tyr Tyr Pro Asp
        35                  40                  45

Lys Val Phe Arg Ser Ser Val Leu His Ser Thr Gln Asp Leu Phe Leu
    50                  55                  60

Pro Phe Phe Ser Asn Val Thr Trp Phe His Ala Ile His Val Ser Gly
65                  70                  75                  80

Thr Asn Gly Thr Lys Arg Phe Asp Asn Pro Val Leu Pro Phe Asn Asp
                85                  90                  95

Gly Val Tyr Phe Ala Ser Thr Glu Lys Ser Asn Ile Ile Arg Gly Trp
            100                 105                 110

Ile Phe Gly Thr Thr Leu Asp Ser Lys Thr Gln Ser Leu Leu Ile Val
        115                 120                 125

Asn Asn Ala Thr Asn Val Val Ile Lys Val Cys Glu Phe Gln Phe Cys
    130                 135                 140

Asn Asp Pro Phe Leu Gly Val Tyr Tyr His Lys Asn Asn Lys Ser Trp
145                 150                 155                 160

Met Glu Ser Glu Phe Arg Val Tyr Ser Ser Ala Asn Asn Cys Thr Phe
                165                 170                 175

Glu Tyr Val Ser Gln Pro Phe Leu Met Asp Leu Glu Gly Lys Gln Gly
            180                 185                 190

Asn Phe Lys Asn Leu Arg Glu Phe Val Phe Lys Asn Ile Asp Gly Tyr
        195                 200                 205

Phe Lys Ile Tyr Ser Lys His Thr Pro Ile Asn Leu Val Arg Asp Leu
    210                 215                 220

Pro Gln Gly Phe Ser Ala Leu Glu Pro Leu Val Asp Leu Pro Ile Gly
225                 230                 235                 240

Ile Asn Ile Thr Arg Phe Gln Thr Leu Leu Ala Leu His Arg Ser Tyr
                245                 250                 255

Leu Thr Pro Gly Asp Ser Ser Ser Gly Trp Thr Ala Gly Ala Ala Ala
            260                 265                 270

Tyr Tyr Val Gly Tyr Leu Gln Pro Arg Thr Phe Leu Leu Lys Tyr Asn
        275                 280                 285
```

-continued

```
Glu Asn Gly Thr Ile Thr Asp Ala Val Asp Cys Ala Leu Asp Pro Leu
290                 295                 300
Ser Glu Thr Lys Cys Thr Leu Lys Ser Phe Thr Val Glu Lys Gly Ile
305                 310                 315                 320
Tyr Gln Thr Ser Asn Phe Arg Val Gln Pro Thr Glu Ser Ile Val Arg
                325                 330                 335
Phe Pro Asn Ile Thr Asn Leu Cys Pro Phe Gly Glu Val Phe Asn Ala
                340                 345                 350
Thr Arg Phe Ala Ser Val Tyr Ala Trp Asn Arg Lys Arg Ile Ser Asn
            355                 360                 365
Cys Val Ala Asp Tyr Ser Val Leu Tyr Asn Ser Ala Ser Phe Ser Thr
370                 375                 380
Phe Lys Cys Tyr Gly Val Ser Pro Thr Lys Leu Asn Asp Leu Cys Phe
385                 390                 395                 400
Thr Asn Val Tyr Ala Asp Ser Phe Val Ile Arg Gly Asp Glu Val Arg
                405                 410                 415
Gln Ile Ala Pro Gly Gln Thr Gly Lys Ile Ala Asp Tyr Asn Tyr Lys
                420                 425                 430
Leu Pro Asp Asp Phe Thr Gly Cys Val Ile Ala Trp Asn Ser Asn Asn
            435                 440                 445
Leu Asp Ser Lys Val Gly Gly Asn Tyr Asn Tyr Leu Tyr Arg Leu Phe
450                 455                 460
Arg Lys Ser Asn Leu Lys Pro Phe Glu Arg Asp Ile Ser Thr Glu Ile
465                 470                 475                 480
Tyr Gln Ala Gly Ser Thr Pro Cys Asn Gly Val Glu Gly Phe Asn Cys
                485                 490                 495
Tyr Phe Pro Leu Gln Ser Tyr Gly Phe Gln Pro Thr Asn Gly Val Gly
                500                 505                 510
Tyr Gln Pro Tyr Arg Val Val Val Leu Ser Phe Glu Leu Leu His Ala
            515                 520                 525
Pro Ala Thr Val Cys Gly Pro Lys Lys Ser Thr Asn Leu Val Lys Asn
530                 535                 540
Lys Cys Val Asn Phe Asn Phe Asn Gly Leu Thr Gly Thr Gly Val Leu
545                 550                 555                 560
Thr Glu Ser Asn Lys Lys Phe Leu Pro Phe Gln Gln Phe Gly Arg Asp
                565                 570                 575
Ile Ala Asp Thr Thr Asp Ala Val Arg Asp Pro Gln Thr Leu Glu Ile
                580                 585                 590
Leu Asp Ile Thr Pro Cys Ser Phe Gly Gly Val Ser Val Ile Thr Pro
            595                 600                 605
Gly Thr Asn Thr Ser Asn Gln Val Ala Val Leu Tyr Gln Asp Val Asn
610                 615                 620
Cys Thr Glu Val Pro Val Ala Ile His Ala Asp Gln Leu Thr Pro Thr
625                 630                 635                 640
Trp Arg Val Tyr Ser Thr Gly Ser Asn Val Phe Gln Thr Arg Ala Gly
                645                 650                 655
Cys Leu Ile Gly Ala Glu His Val Asn Asn Ser Tyr Glu Cys Asp Ile
                660                 665                 670
Pro Ile Gly Ala Gly Ile Cys Ala Ser Tyr Gln Thr Gln Thr Asn Ser
            675                 680                 685
Pro Arg Arg Ala Arg Ser
690
```

<210> SEQ ID NO 7
<211> LENGTH: 290
<212> TYPE: PRT
<213> ORGANISM: Artificial Sequence
<220> FEATURE:
<223> OTHER INFORMATION: SK-E-S1-T1-P2

<400> SEQUENCE: 7

```
Met Gln Tyr Ile Lys Ala Asn Ser Lys Phe Ile Gly Ile Thr Glu Leu
1               5                   10                  15

Gly Ser Gly Ser Gly Thr Glu Ser Ile Val Arg Phe Pro Asn Ile Thr
                20                  25                  30

Asn Leu Cys Pro Phe Gly Glu Val Phe Asn Ala Thr Arg Phe Ala Ser
            35                  40                  45

Val Tyr Ala Trp Asn Arg Lys Arg Ile Ser Asn Cys Val Ala Asp Tyr
        50                  55                  60

Ser Val Leu Tyr Asn Ser Ala Ser Phe Ser Thr Phe Lys Cys Tyr Gly
65                  70                  75                  80

Val Ser Pro Thr Lys Leu Asn Asp Leu Cys Phe Thr Asn Val Tyr Ala
                85                  90                  95

Asp Ser Phe Val Ile Arg Gly Asp Glu Val Arg Gln Ile Ala Pro Gly
            100                 105                 110

Gln Thr Gly Lys Ile Ala Asp Tyr Asn Tyr Lys Leu Pro Asp Asp Phe
        115                 120                 125

Thr Gly Cys Val Ile Ala Trp Asn Ser Asn Asn Leu Asp Ser Lys Val
130                 135                 140

Gly Gly Asn Tyr Asn Tyr Leu Tyr Arg Leu Phe Arg Lys Ser Asn Leu
145                 150                 155                 160

Lys Pro Phe Glu Arg Asp Ile Ser Thr Glu Ile Tyr Gln Ala Gly Ser
                165                 170                 175

Thr Pro Cys Asn Gly Val Glu Gly Phe Asn Cys Tyr Phe Pro Leu Gln
            180                 185                 190

Ser Tyr Gly Phe Gln Pro Thr Asn Gly Val Gly Tyr Gln Pro Tyr Arg
        195                 200                 205

Val Val Val Leu Ser Phe Glu Leu Leu His Ala Pro Ala Thr Val Cys
    210                 215                 220

Gly Pro Lys Lys Ser Thr Asn Leu Val Lys Asn Lys Cys Val Asn Phe
225                 230                 235                 240

Asn Phe Asn Gly Leu Thr Gly Thr Gly Val Leu Thr Glu Ser Asn Lys
                245                 250                 255

Lys Phe Leu Pro Phe Gln Gln Phe Gly Arg Asp Ile Ala Asp Thr Thr
            260                 265                 270

Asp Ala Val Arg Asp Pro Gln Thr Leu Glu Ile Leu Asp Ile Thr Pro
        275                 280                 285

Cys Ser
    290
```

<210> SEQ ID NO 8
<211> LENGTH: 238
<212> TYPE: PRT
<213> ORGANISM: Artificial Sequence
<220> FEATURE:
<223> OTHER INFORMATION: SK-E-RBD-Ex3-P2

<400> SEQUENCE: 8

```
Met Gln Tyr Ile Lys Ala Asn Ser Lys Phe Ile Gly Ile Thr Glu Leu
1               5                   10                  15
```

-continued

Gly Ser Gly Ser Gly Gln Pro Thr Glu Ser Ile Val Arg Phe Pro Asn
            20                  25                  30

Ile Thr Asn Leu Cys Pro Phe Gly Glu Val Phe Asn Ala Thr Arg Phe
        35                  40                  45

Ala Ser Val Tyr Ala Trp Asn Arg Lys Arg Ile Ser Asn Cys Val Ala
    50                  55                  60

Asp Tyr Ser Val Leu Tyr Asn Ser Ala Ser Phe Ser Thr Phe Lys Cys
65                  70                  75                  80

Tyr Gly Val Ser Pro Thr Lys Leu Asn Asp Leu Cys Phe Thr Asn Val
                85                  90                  95

Tyr Ala Asp Ser Phe Val Ile Arg Gly Asp Glu Val Arg Gln Ile Ala
            100                 105                 110

Pro Gly Gln Thr Gly Lys Ile Ala Asp Tyr Asn Tyr Lys Leu Pro Asp
        115                 120                 125

Asp Phe Thr Gly Cys Val Ile Ala Trp Asn Ser Asn Asn Leu Asp Ser
    130                 135                 140

Lys Val Gly Gly Asn Tyr Asn Tyr Leu Tyr Arg Leu Phe Arg Lys Ser
145                 150                 155                 160

Asn Leu Lys Pro Phe Glu Arg Asp Ile Ser Thr Glu Ile Tyr Gln Ala
                165                 170                 175

Gly Ser Thr Pro Cys Asn Gly Val Glu Gly Phe Asn Cys Tyr Phe Pro
            180                 185                 190

Leu Gln Ser Tyr Gly Phe Gln Pro Thr Asn Gly Val Gly Tyr Gln Pro
        195                 200                 205

Tyr Arg Val Val Val Leu Ser Phe Glu Leu Leu His Ala Pro Ala Thr
    210                 215                 220

Val Cys Gly Pro Lys Lys Ser Thr Asn Leu Val Lys Asn Lys
225                 230                 235

<210> SEQ ID NO 9
<211> LENGTH: 202
<212> TYPE: PRT
<213> ORGANISM: Artificial Sequence
<220> FEATURE:
<223> OTHER INFORMATION: SK-E-RBD-P2

<400> SEQUENCE: 9

Met Gln Tyr Ile Lys Ala Asn Ser Lys Phe Ile Gly Ile Thr Glu Leu
1               5                   10                  15

Gly Ser Gly Ser Gly Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

```
Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu
            195                 200
```

<210> SEQ ID NO 10
<211> LENGTH: 270
<212> TYPE: PRT
<213> ORGANISM: Artificial Sequence
<220> FEATURE:
<223> OTHER INFORMATION: SK-E-RBD-Ex3-foldon-P2

<400> SEQUENCE: 10

```
Met Gln Tyr Ile Lys Ala Asn Ser Lys Phe Ile Gly Ile Thr Glu Leu
1               5                   10                  15

Gly Ser Gly Ser Gly Gln Pro Thr Glu Ser Ile Val Arg Phe Pro Asn
                20                  25                  30

Ile Thr Asn Leu Cys Pro Phe Gly Glu Val Phe Asn Ala Thr Arg Phe
            35                  40                  45

Ala Ser Val Tyr Ala Trp Asn Arg Lys Arg Ile Ser Asn Cys Val Ala
        50                  55                  60

Asp Tyr Ser Val Leu Tyr Asn Ser Ala Ser Phe Ser Thr Phe Lys Cys
65                  70                  75                  80

Tyr Gly Val Ser Pro Thr Lys Leu Asn Asp Leu Cys Phe Thr Asn Val
                85                  90                  95

Tyr Ala Asp Ser Phe Val Ile Arg Gly Asp Glu Val Arg Gln Ile Ala
            100                 105                 110

Pro Gly Gln Thr Gly Lys Ile Ala Asp Tyr Asn Tyr Lys Leu Pro Asp
        115                 120                 125

Asp Phe Thr Gly Cys Val Ile Ala Trp Asn Ser Asn Asn Leu Asp Ser
130                 135                 140

Lys Val Gly Gly Asn Tyr Asn Tyr Leu Tyr Arg Leu Phe Arg Lys Ser
145                 150                 155                 160

Asn Leu Lys Pro Phe Glu Arg Asp Ile Ser Thr Glu Ile Tyr Gln Ala
                165                 170                 175

Gly Ser Thr Pro Cys Asn Gly Val Glu Gly Phe Asn Cys Tyr Phe Pro
            180                 185                 190

Leu Gln Ser Tyr Gly Phe Gln Pro Thr Asn Gly Val Gly Tyr Gln Pro
        195                 200                 205

Tyr Arg Val Val Val Leu Ser Phe Glu Leu Leu His Ala Pro Ala Thr
210                 215                 220

Val Cys Gly Pro Lys Lys Ser Thr Asn Leu Val Lys Asn Lys Gly Ser
225                 230                 235                 240

Gly Gly Ser Gly Tyr Ile Pro Glu Ala Pro Arg Asp Gly Gln Ala Tyr
                245                 250                 255

Val Arg Lys Asp Gly Glu Trp Val Leu Leu Ser Thr Phe Leu
            260                 265                 270
```

<210> SEQ ID NO 11
<211> LENGTH: 2085
<212> TYPE: DNA
<213> ORGANISM: Artificial Sequence
<220> FEATURE:

<223> OTHER INFORMATION: the optimized codon of SK-E-S1-P2

<400> SEQUENCE: 11

| | |
|---|---|
| atgcagtata taaaagcaaa ttctaaattt ataggtataa ctgaactagg ctccggctca | 60 |
| ggccagtgtg ttaatcttac aaccagaact caattacccc ctgcatacac taattctttc | 120 |
| acacgtggtg tttattaccc tgacaaagtt ttcagatcct cagttttaca ttcaactcag | 180 |
| gacttgttct tacctttctt ttccaatgtt acttggttcc atgctataca tgtctctggg | 240 |
| accaatggta ctaagaggtt tgataaccct gtcctaccat taatgatgg tgtttatttt | 300 |
| gcttccactg agaagtctaa cataataaga ggctggattt ttggtactac tttagattcg | 360 |
| aagacccagt ccctacttat tgttaataac gctactaatg ttgttattaa agtctgtgaa | 420 |
| tttcaatttt gtaatgatcc attttgggt gtttattacc acaaaaacaa caaaagttgg | 480 |
| atggaaagtg agttcagagt ttattctagt gcgaataatt gcacttttga atatgtctct | 540 |
| cagccttttc ttatggacct tgaaggaaaa cagggtaatt tcaaaaatct tagggaattt | 600 |
| gtgtttaaga atattgatgg ttattttaaa atatattcta agcacacgcc tattaattta | 660 |
| gtgcgtgatc tccctcaggg ttttcggct ttagaaccat tggtagattt gccaataggt | 720 |
| attaacatca ctaggtttca aactttactt gctttacata gaagttattt gactcctggt | 780 |
| gattcttctt caggttggac agctggtgct gcagcttatt atgtgggtta tcttcaacct | 840 |
| aggactttc tattaaaata taatgaaaat ggaaccatta cagatgctgt agactgtgca | 900 |
| cttgacccctc tctcagaaac aaagtgtacg ttgaaatcct tcactgtaga aaaggaatc | 960 |
| tatcaaactt ctaactttag agtccaacca acagaatcta ttgttagatt tcctaatatt | 1020 |
| acaaacttgt gccctttgg tgaagttttt aacgccacca gatttgcatc tgtttatgct | 1080 |
| tggaacagga gagaatcag caactgtgtt gctgattatt ctgtcctata taattccgca | 1140 |
| tcatttttcca cttttaagtg ttatggagtg tctcctacta aattaaatga tctctgctt | 1200 |
| actaatgtct atgcagattc atttgtaatt agaggtgatg aagtcagaca aatcgctcca | 1260 |
| gggcaaactg gaaagattgc tgattataat tataaattac cagatgatt tacaggctgc | 1320 |
| gttatagctt ggaattctaa caatcttgat tctaaggttg gtggtaatta taattacctg | 1380 |
| tatagattgt taggaagtc taatctcaaa ccttttgaga gagatatttc aactgaaatc | 1440 |
| tatcaggccg gtagcacacc ttgtaatggt gttgaaggtt ttaattgtta ctttccttta | 1500 |
| caatcttatg gtttccaacc cactaatggt gttggttacc aaccatacag agtagtagta | 1560 |
| ctttctttg aacttctaca tgcaccagca actgtttgtg gacctaaaaa gtctactaat | 1620 |
| ttggttaaaa acaaatgtgt caatttcaac ttcaatggtt taacaggcac aggtgttctt | 1680 |
| actgagtcta acaaaaagtt tctgcctttc caacaatttg gcagagacat tgctgacact | 1740 |
| actgatgctg tccgtgatcc acagacactt gagattcttg acattacacc atgttctttt | 1800 |
| ggtggtgtca gtgttataac accaggaaca aatacttcta accaggttgc tgttctttat | 1860 |
| caggatgtta actgcacaga agtccctgtt gctattcatg cagatcaact tactcctact | 1920 |
| tggcgtgttt attctacagg ttctaatgtt tttcaaacac gtgcaggctg tttaataggg | 1980 |
| gctgaacatg tcaacaactc ttatgagtgt gacatacca ttggtgcagg tatatgcgct | 2040 |
| agttatcaga ctcagactaa ttctcctcgg cgggcacgta gttga | 2085 |

<210> SEQ ID NO 12
<211> LENGTH: 873
<212> TYPE: DNA
<213> ORGANISM: Artificial Sequence
<220> FEATURE:
<223> OTHER INFORMATION: the optimized codon of SK-E-S1-T1-P2

<400> SEQUENCE: 12

| | |
|---|---|
| atgcagtata taaaagcaaa ttctaaattt ataggtataa ctgaactagg ctccggctca | 60 |
| ggcaccgaaa gcattgttcg tttcccgaac atcaccaacc tgtgcccgtt tggcgaggtg | 120 |
| ttcaacgcga cccgtttcgc gagcgtttat gcgtggaacc gtaaacgtat cagcaactgc | 180 |
| gttgcggatt atagcgtgct gtacaacagc gcgagcttca gcacctttaa gtgctatggt | 240 |
| gttagcccga ccaaactgaa cgacctgtgc tttaccaacg tttacgcgga tagcttcgtg | 300 |
| attcgtggcg acgaagttcg tcagatcgcg ccgggtcaaa ccgcaagat tgcggattac | 360 |
| aactataaac tgccggacga tttcaccggt tgcgtgattg cgtggaacag caacaacctg | 420 |
| gacagcaagg ttggtggcaa ctacaactat ctgtaccgtc tgtttcgtaa gagcaacctg | 480 |
| aaaccgttcg agcgtgatat tagcaccgaa atctaccagg cgggtagcac cccgtgcaac | 540 |
| ggtgtggaag ctttaactg ctatttcccg ctgcagagct acggctttca accgaccaac | 600 |
| ggtgttggct atcaaccgta ccgtgtggtt gttctgagct cgagctgct gcatgcgccg | 660 |
| gcgaccgttt gcggtccgaa gaaaagcacc aacctggtta agaacaaatg cgtgaacttc | 720 |
| aactttaacg gcctgaccgg caccggtgtg ctgaccgaaa gcaacaagaa attcctgccg | 780 |
| tttcagcaat tcggtcgtga catcgcggat accaccgacg cggttcgtga tccgcagacc | 840 |
| ctggagattc tggacatcac cccgtgcagc taa | 873 |

<210> SEQ ID NO 13
<211> LENGTH: 714
<212> TYPE: DNA
<213> ORGANISM: Artificial Sequence
<220> FEATURE:
<223> OTHER INFORMATION: the optimized codon of SK-E-RBD-Ex3-P2

<400> SEQUENCE: 13

| | |
|---|---|
| atgcagtata taaaagcaaa ttctaaattt ataggtataa ctgaactagg ctccggctca | 60 |
| ggccaaccga ccgaaagcat tgttcgtttc ccgaacatca ccaacctgtg cccgtttggc | 120 |
| gaggtgttca cgcgacccg tttcgcgagc gtttatgcgt ggaaccgtaa acgtatcagc | 180 |
| aactgcgttg cggattatag cgtgctgtac aacagcgcga gcttcagcac ctttaagtgc | 240 |
| tatggtgtta gcccgaccaa actgaacgac ctgtgcttta ccaacgttta cgcggatagc | 300 |
| ttcgtgattc gtggcgacga agttcgtcag atcgcgccgg tcaaaccgg caagattgcg | 360 |
| gattacaact ataaactgcc ggacgatttc accggttgcg tgattgcgtg gaacagcaac | 420 |
| aacctggaca gcaaggttgg tggcaactac aactatctgt accgtctgtt tcgtaagagc | 480 |
| aacctgaaac cgttcgagcg tgatattagc accgaaatct accaggcggg tagcaccccg | 540 |
| tgcaacggtg tggaaggctt taactgctat ttcccgctgc agagctacgg ctttcaaccg | 600 |
| accaacggtg ttggctatca accgtaccgt gtggttgttc tgagcttcga gctgctgcat | 660 |
| gcgccggcga ccgtttgcgg tccgaagaaa agcaccaacc tggttaagaa caaa | 714 |

<210> SEQ ID NO 14
<211> LENGTH: 609
<212> TYPE: DNA
<213> ORGANISM: Artificial Sequence
<220> FEATURE:
<223> OTHER INFORMATION: the optimized codon of SK-E-RBD-P2

<400> SEQUENCE: 14

```
atgcagtata taaaagcaaa ttctaaattt ataggtataa ctgaactagg ctccggctca        60
ggctgccctt ttggtgaagt ttttaacgcc accagatttg catctgttta tgcttggaac       120
aggaagagaa tcagcaactg tgttgctgat tattctgtcc tatataattc cgcatcattt       180
tccacttttta agtgttatgg agtgtctcct actaaattaa atgatctctg ctttactaat       240
gtctatgcag attcatttgt aattagaggt gatgaagtca gacaaatcgc tcagggcaa        300
actggaaaga ttgctgatta taattataaa ttaccagatg attttacagg ctgcgttata       360
gcttggaatt ctaacaatct tgattctaag gttggtggta attataatta cctgtataga       420
ttgtttagga agtctaatct caaacctttt gagagagata tttcaactga atctatcag        480
gccggtagca cccttgtaa tggtgttgaa ggttttaatt gttactttcc tttacaatct       540
tatggtttcc aacccactaa tggtgttggt taccaaccat acagagtagt agtactttct       600
tttgaataa                                                                609
```

<210> SEQ ID NO 15
<211> LENGTH: 810
<212> TYPE: DNA
<213> ORGANISM: Artificial Sequence
<220> FEATURE:
<223> OTHER INFORMATION: the optimized codon of SK-E-RBD-Ex3-foldon-P2

<400> SEQUENCE: 15

```
atgcagtata taaaagcaaa ttctaaattt ataggtataa ctgaactagg ctccggctca        60
ggccaaccga ccgaaagcat tgttcgtttc ccgaacatca ccaacctgtg cccgtttggc       120
gaggtgttca cgcgacccg tttcgcgagc gtttatgcgt ggaaccgtaa acgtatcagc       180
aactgcgttg cggattatag cgtgctgtac aacagcgcga gcttcagcac ctttaagtgc       240
tatggtgtta gcccgaccaa actgaacgac ctgtgctttta ccaacgttta cgcggatagc       300
ttcgtgattc gtggcgacga agttcgtcag atcgcgccgg gtcaaaccgg caagattgcg       360
gattacaact ataaactgcc ggacgatttc accggttgcg tgattgcgtg aacagcaac       420
aacctggaca gcaaggttgg tggcaactac aactatctgt accgtctgtt tcgtaagagc       480
aacctgaaac cgttcgagcg tgatattagc accgaaatct accaggcggg tagcaccccg       540
tgcaacggtg tggaaggctt taactgctat ttcccgctgc agagctacgg ctttcaaccg       600
accaacggtg ttggctatca accgtaccgt gtggttgttc tgagcttcga gctgctgcat       660
gcgccggcga ccgtttgcgg tccgaagaaa agcaccaacc tggttaagaa caaaggtagc       720
ggtggcagcg gttacatccc tgaagctccc gcgacggac aggcctacgt ccgtaaggac       780
ggagaatggg tactcctgtc tacgttcctg                                        810
```

<210> SEQ ID NO 16
<211> LENGTH: 439
<212> TYPE: PRT
<213> ORGANISM: Artificial Sequence
<220> FEATURE:
<223> OTHER INFORMATION: SK-E-N

<400> SEQUENCE: 16

Met Gln Tyr Ile Lys Ala Asn Ser Lys Phe Ile Gly Ile Thr Glu Leu
1               5                   10                  15

Gly Ser Gly Ser Gly Ser Asp Asn Gly Pro Gln Asn Gln Arg Asn Ala
            20                  25                  30

```
Pro Arg Ile Thr Phe Gly Gly Pro Ser Asp Ser Thr Gly Ser Asn Gln
            35                  40                  45

Asn Gly Glu Arg Ser Gly Ala Arg Ser Lys Gln Arg Arg Pro Gln Gly
 50                  55                  60

Leu Pro Asn Asn Thr Ala Ser Trp Phe Thr Ala Leu Thr Gln His Gly
 65                  70                  75                  80

Lys Glu Asp Leu Lys Phe Pro Arg Gly Gln Gly Val Pro Ile Asn Thr
                 85                  90                  95

Asn Ser Ser Pro Asp Asp Gln Ile Gly Tyr Tyr Arg Arg Ala Thr Arg
            100                 105                 110

Arg Ile Arg Gly Gly Asp Gly Lys Met Lys Asp Leu Ser Pro Arg Trp
            115                 120                 125

Tyr Phe Tyr Tyr Leu Gly Thr Gly Pro Glu Ala Gly Leu Pro Tyr Gly
        130                 135                 140

Ala Asn Lys Asp Gly Ile Ile Trp Val Ala Thr Glu Gly Ala Leu Asn
145                 150                 155                 160

Thr Pro Lys Asp His Ile Gly Thr Arg Asn Pro Ala Asn Asn Ala Ala
                165                 170                 175

Ile Val Leu Gln Leu Pro Gln Gly Thr Thr Leu Pro Lys Gly Phe Tyr
                180                 185                 190

Ala Glu Gly Ser Arg Gly Gly Ser Gln Ala Ser Ser Arg Ser Ser Ser
            195                 200                 205

Arg Ser Arg Asn Ser Ser Arg Asn Ser Thr Pro Gly Ser Ser Arg Gly
            210                 215                 220

Thr Ser Pro Ala Arg Met Ala Gly Asn Gly Gly Asp Ala Ala Leu Ala
225                 230                 235                 240

Leu Leu Leu Leu Asp Arg Leu Asn Gln Leu Glu Ser Lys Met Ser Gly
                245                 250                 255

Lys Gly Gln Gln Gln Gln Gly Gln Thr Val Thr Lys Lys Ser Ala Ala
            260                 265                 270

Glu Ala Ser Lys Lys Pro Arg Gln Lys Arg Thr Ala Thr Lys Ala Tyr
            275                 280                 285

Asn Val Thr Gln Ala Phe Gly Arg Arg Gly Pro Glu Gln Thr Gln Gly
 290                 295                 300

Asn Phe Gly Asp Gln Glu Leu Ile Arg Gln Gly Thr Asp Tyr Lys His
305                 310                 315                 320

Trp Pro Gln Ile Ala Gln Phe Ala Pro Ser Ala Ser Ala Phe Phe Gly
                325                 330                 335

Met Ser Arg Ile Gly Met Glu Val Thr Pro Ser Gly Thr Trp Leu Thr
            340                 345                 350

Tyr Thr Gly Ala Ile Lys Leu Asp Asp Lys Asp Pro Asn Phe Lys Asp
            355                 360                 365

Gln Val Ile Leu Leu Asn Lys His Ile Asp Ala Tyr Lys Thr Phe Pro
370                 375                 380

Pro Thr Glu Pro Lys Lys Asp Lys Lys Lys Ala Asp Glu Thr Gln
385                 390                 395                 400

Ala Leu Pro Gln Arg Gln Lys Lys Gln Gln Thr Val Thr Leu Leu Pro
            405                 410                 415

Ala Ala Asp Leu Asp Asp Phe Ser Lys Gln Leu Gln Gln Ser Met Ser
            420                 425                 430

Ser Ala Asp Ser Thr Gln Ala
            435
```

<210> SEQ ID NO 17
<211> LENGTH: 2022
<212> TYPE: DNA
<213> ORGANISM: Artificial Sequence
<220> FEATURE:
<223> OTHER INFORMATION: the nucleotide sequences encoding the fragment from 14 to 686 amino acids of S protein

<400> SEQUENCE: 17

```
caatgcgtta atctgaccac ccgcacccaa ctgccgccgg cgtacaccaa tagcttcacc      60
cgtggcgttt actacccgga caaggttttc cgtagcagcg tgctgcacag cacccaggac     120
ctgtttctgc cgttctttag caacgtgacc tggttccacg cgatccacgt tagcggcacc     180
aacggcacca aacgttttga taacccggtg ctgccgttta cgacggtgt ttacttcgcg      240
agcaccgaaa agagcaacat cattcgtggt tggattttcg gcaccaccct ggatagcaaa     300
acccagagcc tgctgatcgt gaacaacgcg accaacgtgg ttattaaggt ttgcgagttc     360
caattttgca cgacccgtt tctgggcgtg tactatcaca agaacaacaa aagctggatg      420
gagagcgagt ccgtgtgta tagcagcgcg aacaactgca cctttgagta cgttagccag     480
ccgttcctga tggatctgga aggcaagcaa ggcaacttta aaaacctgcg tgagttcgtt     540
ttcaagaaca tcgacggtta cttcaaaatc tacagcaaac acccccgat caacctggtg      600
cgtgatctgc cgcagggttt tagcgcgctg gaaccgctgg ttgacctgcc gatcggcatt     660
aacatcaccc gtttccaaac cctgctggcg ctgcaccgta gctacctgac cccgggtgac     720
agcagcagcg gttggaccgc gggtgctgcg gcgtactatg tgggttatct gcagccgcgt     780
accttctctg ctgaaataca cgagaacggc accatcaccg atgcggtgga ttgcgcgctg     840
gacccgctga cgaaaccaa gtgcacccct aagagcttca ccgttgagaa gggtatttac      900
cagaccagca actttcgtgt gcaaccgacc gaaagcattg ttcgtttccc gaacatcacc     960
aacctgtgcc cgtttggcga ggtgttcaac gcgacccgtt tcgcgagcgt ttatgcgtgg    1020
aaccgtaaac gtatcagcaa ctgcgttgcg gattatagcg tgctgtacaa cagcgcgagc    1080
ttcagcacct ttaagtgcta tggtgttagc ccgaccaaac tgaacgacct gtgctttacc    1140
aacgtttacg cggatagctt cgtgattcgt ggcgacgaag tcgtcagat cgcgccgggt     1200
caaaccggca agattgcgga ttacaactat aaactgccgg acgatttcac cggttgcgtg    1260
attgcgtgga acagcaacaa cctggacagc aaggttggtg gcaactacaa ctatctgtac    1320
cgtctgtttc gtaagagcaa cctgaaaccg ttcgagcgtg atattagcac cgaaatctac    1380
caggcgggta gcaccccgtg caacggtgtg gaaggcttta actgctatttt cccgctgcag    1440
agctacggct tcaaccgac caacggtgtt ggctatcaac cgtaccgtgt ggttgttctg    1500
agcttcgagc tgctgcatgc gccggcgacc gtttgcggtc cgaagaaaag caccaacctg    1560
gttaagaaca aatgcgtgaa cttcaacttt aacggcctga ccggcaccgg tgtgctgacc    1620
gaaagcaaca gaaattcct gccgtttcag caattcggtc gtgacatcgc ggataccacc    1680
gacgcggttc gtgatccgca gaccctggag attctggaca tcacccgtg cagctttggt    1740
ggcgttagcg tgatcacccc gggcaccaac accagcaacc aggttgcggt gctgtatcaa    1800
gatgtgaact gcaccgaggt tccggtggcg attcatgcgg accagctgac cccgacctgg    1860
cgtgtgtaca gcaccggtag caacgttttc caaacccgtg cgggttgcct gattggtgcg    1920
gagcacgtta acaacagcta tgaatgcgac attccgatcg gcgcgggtat ttgcgcgagc    1980
tatcagaccc agaccaacag cccgcgtcgt gcgcgtagct aa                        2022
```

<210> SEQ ID NO 18
<211> LENGTH: 807
<212> TYPE: DNA
<213> ORGANISM: Artificial Sequence
<220> FEATURE:
<223> OTHER INFORMATION: the nucleotide sequences encoding the fragment
      from 323 to 591 amino acids of S protein

<400> SEQUENCE: 18

| | | | | | |
|---|---|---|---|---|---|
| accgaaagca | ttgttcgttt | cccgaacatc | accaacctgt | gcccgtttgg | cgaggtgttc | 60 |
| aacgcgaccc | gtttcgcgag | cgtttatgcg | tggaaccgta | aacgtatcag | caactgcgtt | 120 |
| gcggattata | gcgtgctgta | caacagcgcg | agcttcagca | cctttaagtg | ctatggtgtt | 180 |
| agcccgacca | aactgaacga | cctgtgcttt | accaacgttt | acgcggatag | cttcgtgatt | 240 |
| cgtggcgacg | aagttcgtca | gatcgcgccg | ggtcaaaccg | gcaagattgc | ggattacaac | 300 |
| tataaactgc | cggacgattt | caccggttgc | gtgattgcgt | ggaacagcaa | caacctggac | 360 |
| agcaaggttg | gtggcaacta | caactatctg | taccgtctgt | ttcgtaagag | caacctgaaa | 420 |
| ccgttcgagc | gtgatattag | caccgaaatc | taccaggcgg | gtagcacccc | gtgcaacggt | 480 |
| gtggaaggct | taactgctat | ttcccgctg | cagagctacg | gctttcaacc | gaccaacggt | 540 |
| gttggctatc | aaccgtaccg | tgtggttgtt | ctgagcttcg | agctgctgca | tgcgccggcg | 600 |
| accgtttgcg | gtccgaagaa | aagcaccaac | ctggttaaga | acaaatgcgt | gaacttcaac | 660 |
| tttaacggcc | tgaccggcac | cggtgtgctg | accgaaagca | caagaaatt | cctgccgttt | 720 |
| cagcaattcg | gtcgtgacat | cgcggatacc | accgacgcgg | ttcgtgatcc | gcagaccctg | 780 |
| gagattctgg | acatcacccc | gtgcagc | | | | 807 |

<210> SEQ ID NO 19
<211> LENGTH: 651
<212> TYPE: DNA
<213> ORGANISM: Artificial Sequence
<220> FEATURE:
<223> OTHER INFORMATION: the nucleotide sequences encoding the fragment
      from 321 to 537 amino acids of S protein

<400> SEQUENCE: 19

| | | | | | |
|---|---|---|---|---|---|
| caaccgaccg | aaagcattgt | tcgtttcccg | aacatcacca | acctgtgccc | gtttggcgag | 60 |
| gtgttcaacg | cgacccgttt | cgcgagcgtt | tatgcgtgga | accgtaaacg | tatcagcaac | 120 |
| tgcgttgcgg | attatagcgt | gctgtacaac | agcgcgagct | tcagcacctt | taagtgctat | 180 |
| ggtgttagcc | cgaccaaact | gaacgacctg | tgctttacca | acgtttacgc | ggatagcttc | 240 |
| gtgattcgtg | gcgacgaagt | tcgtcagatc | gcgccgggtc | aaaccggcaa | gattgcggat | 300 |
| tacaactata | aactgccgga | cgatttcacc | ggttgcgtga | ttgcgtggaa | cagcaacaac | 360 |
| ctggacagca | aggttggtgg | caactacaac | tatctgtacc | gtctgtttcg | taagagcaac | 420 |
| ctgaaaccgt | tcgagcgtga | tattagcacc | gaaatctacc | aggcgggtag | caccccgtgc | 480 |
| aacggtgtgg | aaggctttaa | ctgctatttc | ccgctgcaga | gctacggctt | tcaaccgacc | 540 |
| aacggtgttg | gctatcaacc | gtaccgtgtg | gttgttctga | gcttcgagct | gctgcatgcg | 600 |
| ccggcgaccg | tttgcggtcc | gaagaaaagc | accaacctgg | ttaagaacaa | a | 651 |

<210> SEQ ID NO 20
<211> LENGTH: 543
<212> TYPE: DNA
<213> ORGANISM: Artificial Sequence
<220> FEATURE:
<223> OTHER INFORMATION: the nucleotide sequences encoding the fragment
      from 336 to 516 amino acids of S prot

<400> SEQUENCE: 20

```
tgcccgtttg gcgaggtgtt caacgcgacc cgtttcgcga gcgtttatgc gtggaaccgt    60
aaacgtatca gcaactgcgt tgcggattat agcgtgctgt acaacagcgc gagcttcagc   120
acctttaagt gctatggtgt tagcccgacc aaactgaacg acctgtgctt taccaacgtt   180
tacgcggata gcttcgtgat tcgtggcgac gaagttcgtc agatcgcgcc gggtcaaacc   240
ggcaagattg cggattacaa ctataaactg ccggacgatt tcaccggttg cgtgattgcg   300
tggaacagca acaacctgga cagcaaggtt ggtggcaact acaactatct gtaccgtctg   360
tttcgtaaga gcaacctgaa accgttcgag cgtgatatta gcaccgaaat ctaccaggcg   420
ggtagcaccc cgtgcaacgg tgtggaaggc tttaactgct atttcccgct gcagagctac   480
ggctttcaac cgaccaacgg tgttggctat caaccgtacc gtgtggttgt tctgagcttc   540
gag                                                                 543
```

<210> SEQ ID NO 21
<211> LENGTH: 27
<212> TYPE: PRT
<213> ORGANISM: Artificial Sequence
<220> FEATURE:
<223> OTHER INFORMATION: foldon domain

<400> SEQUENCE: 21

```
Gly Tyr Ile Pro Glu Ala Pro Arg Asp Gly Gln Ala Tyr Val Arg Lys
1               5                   10                  15
Asp Gly Glu Trp Val Leu Leu Ser Thr Phe Leu
            20                  25
```

<210> SEQ ID NO 22
<211> LENGTH: 1260
<212> TYPE: DNA
<213> ORGANISM: Artificial Sequence
<220> FEATURE:
<223> OTHER INFORMATION: the optimized codon of SK-E-N

<400> SEQUENCE: 22

```
atgtctgata atggaccccca aaatcagcga atgcacccc gcattacgtt tggtggaccc    60
tcagattcaa ctggcagtaa ccagaatgga gaacgcagtg gggcgcgatc aaaacaacgt   120
cggccccaag gtttacccaa taatactgcg tcttggttca ccgctctcac tcaacatggc   180
aaggaagacc ttaaattccc tcgaggacaa ggcgttccaa ttaacaccaa tagcagtcca   240
gatgaccaaa ttggctacta ccgaagagct accagacgaa ttcgtggtgg tgacggtaaa   300
atgaaagatc tcagtccaag atggtatttc tactacctag gaactgggcc agaagctgga   360
cttccctatg gtgctaacaa agacggcatc atttggttg caactgaggg agccttgaat   420
acaccaaaag atcacattgg cacccgcaat cctgctaaca atgctgcaat cgtgctacaa   480
cttcctcaag gaacaacatt gccaaaaggc ttctacgcag aagggagcag aggcggcagt   540
caagcctctt ctcgttcctc atcacgtagt cgcaacagtt caagaaattc aactccaggc   600
agcagtaggg gaacttctcc tgctagaatg gctggcaatg gcggtgatgc tgctcttgct   660
ttgctgctgc ttgacagatt gaaccagctt gagagcaaaa tgtctggtaa aggccaacaa   720
caacaaggcc aaactgtcac taagaaatct gctgctgagg cttctaagaa gcctcggcaa   780
aaacgtactg ccactaaagc atacaatgta acacaagctt cggcagacg tggtccagaa   840
caaacccaag gaaattttgg ggaccaggaa ctaatcagac aaggaactga ttacaaacat   900
```

-continued

```
tggccgcaaa ttgcacaatt tgcccccagc gcttcagcgt tcttcggaat gtcgcgcatt   960
ggcatggaag tcacaccttc gggaacgtgg ttgacctaca caggtgccat caaattggat   1020
gacaaagatc caaatttcaa agatcaagtc attttgctga ataagcatat tgacgcatac   1080
aaaacattcc caccaacaga gcctaaaaag gacaaaaaga agaaggctga tgaaactcaa   1140
gccttaccgc agagacagaa gaaacagcaa actgtgactc ttcttcctgc tgcagatttg   1200
gatgatttct ccaaacaatt gcaacaatcc atgagcagtg ctgactcaac tcaggcctaa   1260
```

<210> SEQ ID NO 23
<211> LENGTH: 5
<212> TYPE: PRT
<213> ORGANISM: Artificial Sequence
<220> FEATURE:
<223> OTHER INFORMATION: GSGSG linker

<400> SEQUENCE: 23

Gly Ser Gly Ser Gly
1               5

<210> SEQ ID NO 24
<211> LENGTH: 4
<212> TYPE: PRT
<213> ORGANISM: Artificial Sequence
<220> FEATURE:
<223> OTHER INFORMATION: GSSG linker

<400> SEQUENCE: 24

Gly Ser Ser Gly
1

<210> SEQ ID NO 25
<211> LENGTH: 5
<212> TYPE: PRT
<213> ORGANISM: Artificial Sequence
<220> FEATURE:
<223> OTHER INFORMATION: GSGGS linker

<400> SEQUENCE: 25

Gly Ser Gly Gly Ser
1               5

<210> SEQ ID NO 26
<211> LENGTH: 4
<212> TYPE: PRT
<213> ORGANISM: Artificial Sequence
<220> FEATURE:
<223> OTHER INFORMATION: GSGS linker

<400> SEQUENCE: 26

Gly Ser Gly Ser
1

<210> SEQ ID NO 27
<211> LENGTH: 6
<212> TYPE: PRT
<213> ORGANISM: Artificial Sequence
<220> FEATURE:
<223> OTHER INFORMATION: GSGSSG linker

<400> SEQUENCE: 27

Gly Ser Gly Ser Ser Gly
1               5

<210> SEQ ID NO 28

```
<211> LENGTH: 21
<212> TYPE: PRT
<213> ORGANISM: Artificial Sequence
<220> FEATURE:
<223> OTHER INFORMATION: pelB leader sequence

<400> SEQUENCE: 28

Lys Tyr Leu Leu Pro Thr Ala Ala Ala Gly Leu Leu Leu Ala Ala
1               5                   10                  15

Gln Pro Ala Met Ala
            20
```

VACCINE COMPOSITION FOR PREVENTION OR TREATMENT OF SARS-CORONAVIRUS-2 INFECTION

CROSS-REFERENCE TO RELATED APPLICATIONS

This application is a national phase application of PCT Application No. PCT/KR2021/015262, filed on Oct. 27, 2021, which claims benefit of Korean Patent Application No. 10-2020-0141598, filed Oct. 28, 2020. The entire disclosure of the applications identified in this paragraph are incorporated herein by reference.

SEQUENCE LISTING

This application contains references to amino acid sequences and/or nucleic acid sequences which have been submitted concurrently herewith as the sequence listing text file entitled "000076usnp_SequenceListing.txt", file size 48,261 bytes, created on 27 Apr. 2023. The aforementioned sequence listing is hereby incorporated by reference in its entirety pursuant to 37 C.F.R. § 1.52(e)(5).

TECHNICAL FIELD

The present invention relates to a vaccine composition for preventing or treating SARS-coronavirus-2 (SARS-CoV-2) infectious disease, and more specifically, it relates to a vaccine composition for preventing or treating SARS-coronavirus-2 infectious disease using a recombinant protein antigen derived from SARS-coronavirus-2 (SARS-CoV-2).

BACKGROUND ART

SARS-coronavirus-2 (SARS-COV-2) is also called Severe Acute Respiratory Syndrome Coronavirus 2 or COVID19, and in Korea, it is named Corona 19. SARS-coronavirus-2 is a virus first discovered at Huanan Seafood Market in Wuhan on Dec. 12, 2019, and is an RNA virus, and human-to-human infection was confirmed.

SARS-coronavirus-2 is a virus in need of handling in a biosafety level 3 research facility (BSL-3 facility), and the reproduction index (RO) of the virus is estimated as 1.4~3.9. This means that one patient can carry the virus to at least 1.4 people to 3.9 people at maximum, and in other words, it is estimated that control of infectious disease by SARS-coronavirus-2 is significantly difficult, and it was counted that there were 785,867 infected people, and 37,827 deaths worldwide, based on Mar. 31, 2020.

For 2~14 days after infection of the virus, symptoms such as fever, dyspnea, kidney and liver damage, cough, pneumonia and the like are observed, and a therapeutic agent has not been developed yet.

In order to prevent infection, and prevent spread to the community in a situation in which a therapeutic agent has not been developed, research on a vaccine is urgently required. As the corresponding prevalent virus is commonly a high-risk pathogen, in case of inactivated and live vaccines, the risk is high in production and administration into a human body of vaccine materials. In particular, in case of the live vaccine, it takes a very long period of time to an attenuation process and verification of safety. The inventors of the present invention have studied a recombinant protein vaccine applicable to the current pandemic new type of infectious disease in terms of versatility, safety, efficacy, and commercialization, and have completed the present invention.

Many studies on recombinant protein production using Escherichia coli (E. coli) have been conducted so far, and this is because manipulation of Escherichia coli is easy, and there are advantages of short growth time, safe expression, low cost and easily changeable scale. However, it is frequently seen that most proteins form an inclusion body and are degraded by protease, even if the expression level of the expressed protein is low, or it is overexpressed, when a foreign protein is expressed by Escherichia coli. This occurs when the expressed protein is not accurately folded, and it becomes a large obstacle to protein function research. In addition, it may be insufficient for induction of immunogenicity, since it does not form an intact antigen protein structure due to lack of posttranslational processing. In case of the S1 subunit, RBD, truncated S1 and N protein of SARS-COV-2 S protein, they are overexpressed during expression in E. coli, but the amount expressed in a soluble form is extremely limited, and most of them are expressed in an inclusion body form. In order to solve this, it has reached development of a new method which can obtain a SARS-COV-2 antigen protein having intact activity from the overexpressed inclusion body.

DISCLOSURE

Technical Problem

Accordingly, a problem to be solved by the present invention, is to provide a new antigen for preventing or treating infectious disease of SARS-coronavirus-2, a vaccine composition comprising the antigen, or a method for preparation thereof, in order to solve the above problem. The present invention is to provide a recombinant protein vaccine, a method for preventing or treating infectious disease of SARS-coronavirus-2 using the same or a use for preventing or treating SARS-coronavirus-2 infectious disease of the recombinant protein vaccine. In addition, the present invention is to provide a SARS-COV-2 recombinant antigen protein, which is expressed in Escherichia coli (E. coli) and can exhibit function as an antigen.

Technical Solution

In order to solve the above problem, one aspect of the present invention provides a recombinant antigen protein for preventing or treating SARS-coronavirus-2 infection. Preferably, the recombinant antigen protein provides an antigen protein which can be expressed in Escherichia coli (E. coli) and has a three-dimensional structure having intact activity.

One aspect of the present invention provides a recombinant antigen protein for preventing or treating SARS-coronavirus-2 infection, comprising a polypeptide derived from an S1 subunit of a spike protein of SARS-coronavirus-2 and a polypeptide constituting a tetanus toxin (TT) epitope P2 domain. Herein, 'polypeptide derived from an S1 subunit of a spike protein of SARS-coronavirus-2' is used as a meaning of comprising a polypeptide constituting an S1 subunit of a spike protein of SARS-coronavirus-2, or a part of the polypeptide constituting an S1 subunit. A part of the polypeptide constituting an S1 subunit includes that a part of amino acids at the N-terminus and/or C-terminus of the polypeptide constituting an S1 subunit are cut, removed, or modified, and preferably, it includes that a part of amino acids at the N-terminus and/or C-terminus are cut. Hereinafter, the spike protein of SARS-coronavirus-2 is referred to as S protein.

In the recombinant antigen protein of the present invention, each of the polypeptides may be linked by a linker, and the linker includes a peptide linker. The linker may have a length of for example, 16 amino acids or less, and preferably, it may be composed by 6 or less amino acids. The amino acid used for the linker may be at least one of G (Gly, glycine), S (Ser, serine), and A (Ala, alanine), and preferably, it may be at least one peptide linker selected from the group consisting of Gly-Ser-Gly-Ser-Gly (GSGSG, SEQ ID NO: 23), Gly-Ser-Ser-Gly (GSSG, SEQ ID NO: 24), Gly-Ser-Gly-Gly-Ser (GSGGS, SEQ ID NO: 25), Gly-Ser-Gly-Ser (GSGS, SEQ ID NO: 26), and Gly-Ser-Gly-Ser-Ser-Gly (GSGSSG, SEQ ID NO: 27), and the foldon domain and P2 domain in the present description may be linked by the same linker or a different linker, and preferably, on the purpose of the present invention, as a linker between P2 and S protein, GSGSG (SEQ ID NO: 23) may be used, and as that between S protein and foldon, a GSGGS peptide linker (SEQ ID NO: 25) may be used.

SARS-COV-2 is known to strongly attach on the surface of a host cell through an ACE2 (Angiotensin Converting Enzyme2) receptor, and an RBD (Receptor-Binding Domain) of the spike protein of SARS-COV-2 is known to be used for binding to the ACE2 receptor. The RBD is included in the S1 subunit. In one example of the present invention, the RBD comprised in the spike protein of SARS-COV-2 used in the RBD crystal structure is positioned at 336-516 of the full-length amino acid sequence of the spike protein of wild-type SARS-COV-2.

The inventors of the present invention have confirmed that a SARS-COV-2 antigen protein of foreign origin produced in *Escherichia coli* (*E. coli*) has a low expression level, or is difficult to form an intact protein structure, and through the present invention, the expression yield is to be increased in *Escherichia coli* (*E. coli*), and intact disulfide bond formation and functional structure stabilization, and immunogenicity increase of the antigen protein are to be achieved. As an expected effect of SEQ ID NO: 5, an increase of the expressed amount in a soluble form as the RBD of the most compact structure may be expected. SEQ ID NO: 4 has an increase of 15 amino acids at the N-terminus and 21 amino acids at the C-terminus than SEQ ID NO: 5, and during refolding, an additional disulfide bond is formed, and thereby, it may be expected that an additional structure of a beta sheet and a loop is helpful for formation of an intact structure of an antigen. SEQ ID NO: 3 has an increase of 13 amino acids at the N-terminus and 75 amino acids at the C-terminus than SEQ ID NO: 5, so an RBD subdomain is added, and therefore, an increase in immunogenicity according to stabilization of the RBD structure and an increase in the antigen size may be expected. In addition, the recombinant antigen protein obtained through one example of the present invention can increase the adsorption rate to an alum hydroxide gel comprised in an adjuvant or a vaccine formulation, leading to provide a recombinant antigen protein and an expression codon-optimized sequence in *Escherichia coli*, capable of helping an immunogenicity increase.

One example of the present invention comprises a recombinant antigen protein in which a tetanus toxin (TT) epitope P2 domain having SEQ ID NO: 1 and a polypeptide derived from an S1 subunit of a spike protein of SARS-coronavirus-2 having SEQ ID NO: 2 are linked by a GSGSG peptide linker (SEQ ID NO: 23), and the recombinant antigen protein is represented by SEQ ID NO: 6.

The tetanus toxin (TT) epitope P2 domain may be replaced with other T cell epitope peptide, and any T cell epitope domain may be used without limitation. Preferably, as one of the T cell epitope, a Tetanus Toxoid Epitope P2 domain (SEQ ID NO: 1) may be comprised. The P2 domain may exhibit a more enhanced immunostimulating effect by being fused with a protein derived from the S1 subunit of the spike protein (S protein) of SARS-coronavirus-2, and preferably, the P2 domain may be positioned at the N-terminus of the recombinant protein antigen.

In another aspect, the recombinant antigen may be provided in a form in which the polypeptide constituting a P2 domain is fused with 'a polypeptide in which a part of the N-terminus and C-terminus of the polypeptide derived from the S1 subunit are cut'. Preferably, an additional sequence including an RBD domain in the polypeptide sequence constituting the S1 subunit may be further extended at the N-terminus and C-terminus. Preferably, the 'polypeptide in which a part of the N-terminus and C-terminus of the polypeptide constituting the S1 subunit are cut' may have the amino acid sequence corresponding to 321 to 537th positions based on the full-length amino acid sequence of S protein (SEQ ID NO: 4), or have the amino acid sequence corresponding to 323 to 591th position based on the amino acid sequence of S protein (SEQ ID NO: 3), or have the amino acid sequence corresponding to 336 to 516th positions based on the amino acid sequence of S protein (SEQ ID NO: 5). The antigen protein according to one example of the present invention can exclude an undesired disulfide bond, and increase consistency of a disulfide binding pattern, so it can perform its own function and be stably maintained, as the refolding control of protein is easy and protein forms an intact three-dimensional structure. Moreover, a construct expressing a protein having the amino acid sequence can increase a produced amount of protein, and can induce an excellent immune response. In particular, the recombinant protein having SEQ ID NO: 3 can surprisingly stabilize the RBD structure, and an increase in immunogenicity according to the antigen size can be expected. The recombinant protein having SEQ ID NO: 4 can induce formation of an intact disulfide bond, and can increase functional structure formation.

In other one example, the recombinant antigen protein for preventing or treating SARS-coronavirus-2 infection may be provided in a form in which a foldon domain is linked by a linker between the polypeptide constituting a tetanus toxin (TT) epitope P2 domain and the polypeptide derived from an S1 subunit of a spike protein of SARS-coronavirus-2. Preferably, it may be provided as a trimerized domain is linked by a linker between the tetanus toxin (TT) epitope P2 peptide and polypeptide having the amino acid sequence of SEQ ID NO: 4. Preferably, a foldon of bacteriophage T4 fibritin may be comprised, and an example thereof is represented by the amino acid sequence of SEQ ID NO: 21. The foldon domain can increase an antigen size by inducing that an antigen forms a trimer, and because of this, can increase protein stability and increase antigenicity.

The present invention provides a recombinant antigen protein having any one amino acid sequence selected from the group consisting of SEQ ID NOs: 6 to 10.

The term used in the present description, "recombinant antigen protein" is an antigen for preventing or treating SARS-COV-2 infectious disease, and specifically, it means a protein comprising an amino acid sequence of a specific section, selected at a specific position of a spike protein of SARS-COV-2. The recombinant antigen protein means an artificially made protein by cutting of some regions of a spike protein of SARS-CoV-2, binding to a foreign gene, and the like.

The present invention provides a nucleotide sequence encoding the recombinant protein antigen defined above, and provides a gene encoding for expression of a recombinant protein antigen. The gene may consist of any one base sequence selected from SEQ ID NOs: 11 to 15, which are *Escherichia coli* (*E. coli*) codon optimized. "Codon optimization" is a method for enhancing production of protein by highlighting a preferred codon among amino acid codons in a region encoding protein and making it a rare codon, and means changing codons of a polynucleotide encoding protein. Through a gene selected from codon optimized SEQ ID NOs: 11 to 15 obtained in one embodiment of the present invention, a recombinant antigen protein with a high expression rate in *Escherichia coli*, and excellent refolding efficiency of the expressed recombinant antigen protein.

One example of the present invention provides a recombinant vector comprising the gene. Preferably, the recombinant vector comprises any one nucleotide sequence selected from SEQ ID NOs: 11 to 15. DNA molecules comprising a nucleotide sequence encoding the antigen protein of the present invention may be inserted into a vector having transcription and translation regulatory signals. The recombinant antigen protein of the present invention may be prepared by cloning and expression in a prokaryotic expression system, using an appropriate expression vector. Any method known in the art may be used. Preferably, considering the purpose and protein expression rate and the like of the present invention, an *E. coli* expression system may be used. The vector may be any appropriate type, and non-restrictively, the vector which may be used in the present invention may be constructed by manipulating a plasmid commonly used in the art (e.g.: pTrc99A, pSTV28, pSC101, pGV1106, pACYC177, ColE1, pKT230, pME290, pBR322, pUC8/9, pUC6, pBD9, pHC79, pIJ61, pLAFR1, pHV14, pET22b, pGEX series, pET series and pUCP19, etc.), or a phage (e.g.: λgt4·λB, λ-Charon, λΔz1 and M13, etc.) commonly used in the art, and preferably, pET27-b vector may be used. In other embodiment, a nucleotide encoding an *Escherichia coli* pelB leader sequence may be inserted into an expression vector. The pelB leader sequence may have the amino acid sequence of SEQ ID NO: 28. This is one kind of cell membrane gap signal sequences of *Escherichia coli*, and when the SARS-COV-2 recombinant antigen protein of the present invention is synthesized, it may be used on a purpose of inducing an accurate disulfide bond by transferring it into a cell membrane gap of *Escherichia coli*, inhibiting formation of insoluble aggregates of the recombinant antigen protein, and allowing a purification process easy by minimizing unnecessary *E. coli*-derived protein.

The cell stably transformed by the introduced DNA, may be selected also by introducing at least one marker allowing selection of a host cell containing the expression vector. The marker may provide for example, antibiotic resistance, deficient nutrient synthesis genes, and the like. Once a vector or DNA sequence containing the construct is prepared for expression, the DNA construct may be introduced into an appropriate host cell by any one of various appropriate means, that is, transformation, transfection, conjugation, protoplast fusion, electroporation, calcium phosphate-precipitation, direct microinjection and the like.

Other one example provides a host cell for production of a recombinant antigen protein for preventing or treating SARS-coronavirus-2 infectious disease. The term, 'host cell' refers to a cell which can grow in a cultured solution and express a target protein recombinant product protein. Through the host cell, a recombinant antigen protein with an excellent expression rate may be obtained. As a non-restrictive example, within a range which does not hinder the purpose of the present invention, as an example of the eukaryotic host cell, yeasts, algae, plants, *Caenorhabditis elegans* (or nematodes), and the like may be included, and the prokaryotic host cells, may include for example, bacterial cells such as *Escherichia coli* (*E. coli, B. subtilis*), *Salmonella typhi* and mycobacteria, and preferably, *Escherichia coli* (*E. coli*) may be used. After introduction of the vector, the host cell is proliferated in a general medium or a selective medium (selected for growth of cells containing the vector). As a result of expression of the cloned gene sequence(s), a target protein is produced. Purification of the recombinant antigen protein may be performed by any common process accompanying any one of the known methods on the above purpose, that is, extraction, precipitation, chromatography, electrophoresis, and the like. As a host cell capable of cloning and expressing the vector of the present invention into a prokaryotic cell stably and continuously, an *Escherichia coli* cell is preferably, and for example, *E. coli* Rosetta, *E. coli* JM109, *E. coli* BL21, *E. coli* RR1, *E. coli* LE392, *E. coli* B, *E. coli* X 1776, *E. coli* W3110 and the like may be comprised.

Other example of the present invention provides a recombinant gram-negative bacterial cell for production of a recombinant antigen protein for preventing or treating SARS-coronavirus-2 infectious disease. The recombinant gram-negative bacterial cell may have a gene encoding a polypeptide derived from an S1 subunit of a spike protein of SARS-coronavirus-2, a gene encoding a tetanus toxin (TT) epitope P2 peptide, and/or a gene encoding a foldon domain. The recombinant gram-negative bacterial cell may preferably have any one nucleotide sequence selected from the group consisting of SEQ ID NOs: 11 to 15.

Other example of the present invention provides a method for preparation of a transformed *Escherichia coli* for expressing a recombinant SARS-coronavirus-2 antigen protein having any one amino acid sequence selected from the group consisting of SEQ ID NOs: 6 to 10 comprising the following steps. The method for preparation may comprise (a) obtaining any one nucleotide sequence selected from SEQ ID NOs: 11 to 15 by codon optimization of a part of a nucleotide sequence of an S protein of SARS-coronavirus-2 suitable for expression in *Escherichia coli*; (b) inserting the codon optimized nucleotide sequence into an expression vector to prepare a recombinant vector; and (c) introducing the recombinant vector into *Escherichia coli* to prepare the transformed *Escherichia coli*. One example of the present invention provides a recombinant SARS-coronavirus-2 antigen protein prepared by the method for preparation. Preferably, the step (a) is codon optimizing using a nucleotide sequence encoding an S protein of SARS-coronavirus-2, a nucleotide sequence encoding a tetanus toxin (TT) epitope P2 peptide, and selectively, a nucleotide sequence encoding the foldon domain of SEQ ID NO: 21. One example of the present invention provides an *Escherichia coli* cell for expressing a SARS-coronavirus-2 antigen protein prepared by the method.

Other aspect of the present invention provides a method for preparation of the recombinant antigen protein, and the method may comprise culturing a host cell transformed with a vector containing the nucleotide sequence of the present invention, and isolating a target product.

Other embodiment of the present invention provides a new use of the recombinant protein antigen, for preventing or treating SARS-coronavirus-2 infectious disease, and provides a method for preventing SARS-coronavirus-2 infectious disease which prevents or treats SARS-coronavirus-2 infection by administering the antigen into a subject.

Other embodiment of the present invention provides a vaccine composition for preventing or treating SARS-coronavirus-2 infectious disease comprising the recombinant antigen protein according to the present invention as an active ingredient. The 'SARS-coronavirus-2 infectious disease' may be understood as a concept widely comprising not only infection of SARS-coronavirus-2 itself, but also various disease symptoms generated from infection of the virus (for example, respiratory disease, pneumonia, etc.). In the present invention, the vaccine may be prepared by a common method well known in the art, and various additives which can be used during preparation of a vaccine in the art may be further comprised selectively. The vaccine composition according to the present invention may comprise the recombinant antigen protein and a pharmaceutically acceptable carrier. It is not limited thereto, but it includes for example, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil and the like, as one commonly used during preparation, but not limited thereto. The pharmaceutical composition of the present invention may be used by further comprising a non-ionic surfactant such as TWEEN™, polyethylene glycol (PEG) and the like, an antioxidant including ascorbic acid, a lubricant, a wetting agent, a sweetener, a flavoring agent, an emulsifier, a suspending agent, a preservative, and the like, in addition to the above components. In the present invention, the vaccine may be prepared in a unit dose form by formulating using a pharmaceutically acceptable carrier and/or an excipient, or be prepared by inserting into a multi-dose container, according to a method which can be easily conducted by those skilled in the art to which the present invention pertains. Then, the formulation may be in a form of a solution, suspension or emulsion in an oil or aqueous medium, or may be in a form of extract, a powder, a granule, a tablet or a capsule, and a dispersing agent or a stabilizer may be additionally comprised. In the present invention, the appropriate dosage of the vaccine may be variously prescribed by factors such as a formulation method, an administration method, a patient's age, body weight, gender, morbid condition, food, administration time, an administration route, an excretion rate and response sensitivity. On the other hand, the dosage of the vaccine according to the present invention may be preferably 10~100 ug per dose. In one embodiment of the present invention, the vaccine comprising the recombinant antigen protein as an active ingredient may be administered into a body by intravenous injection, intramuscular injection, subcutaneous injection, dermal delivery, or airway inhalation, but not limited thereto.

The vaccine composition may further comprise an immunological adjuvant to improve an immune response effect, and may further comprise a recombinant nucleocapsid (N) protein together with the immunological adjuvant or without an immunological adjuvant.

The immunological adjuvant may be at least one selected from for example, CpG squalene (MF59), liposome, TLR agonist, MPL (monophosphoryl lipid A) (AS04), magnesium hydroxide, magnesium carbonate hydroxide, pentahydrate, titanium dioxide, calcium carbonate, barium oxide, barium hydroxide, barium peroxide, barium sulfate, calcium sulfate, calcium pyrophosphate, magnesium carbonate, magnesium oxide, aluminum hydroxide, aluminum phosphate, and hydrated aluminum potassium sulfate (Alum), but not limited thereto.

The 'recombinant nucleocapsid (N) protein' is represented by SEQ ID NO: 16 and is an artificially made nucleocapsid (N) protein of SARS-coronavirus-2, and is a protein in which an amino acid sequence constituting the nucleocapsid (N) protein of SARS-coronavirus-2 is fused with a P2 domain.

Selectively, the vaccine composition may further comprise an M protein of SARS-coronavirus-2.

Sequence information was shown in Table 1 below.

TABLE 1

| Number | Classification | Note |
| --- | --- | --- |
| 1 | Peptide | Tetanus toxoid P2 epitope peptide |
| 2 | Peptide | 14th-686th amino acids of S protein |
| 3 | Peptide | 323th-591th amino acids of S protein |
| 4 | Peptide | 321th-537th amino acids of S protein S |
| 5 | Peptide | 336th-516th amino acids of S protein |
| 6 | Peptide | SK-E-S1-P2 |
| 7 | Peptide | SK-E-S1-T1-P2 |
| 8 | Peptide | SK-E-RBD-Ex3-P2 |
| 9 | Peptide | SK-E-RBD-P2 |
| 10 | Peptide | SK-E-RBD-Ex3-foldon-P2 |
| 11 | Nucleotide | Codon optimization of SK-E-S1-P2 |
| 12 | Nucleotide | Codon optimization of SK-E-S1-T1-P2 |
| 13 | Nucleotide | Codon optimization of SK-E-RBD-Ex3-P2 |
| 14 | Nucleotide | Codon optimization of SK-E-RBD-P2 |
| 15 | Nucleotide | Codon optimization of SK-E-RBD-Ex3-foldon-P2 |
| 16 | Peptide | Amino acid sequence of SK-E-N |
| 17 | Nucleotide | Nucleotide sequence encoding 14th-686th amino acids of S protein |
| 18 | Nucleotide | Nucleotide sequence encoding 323th-591th amino acids of S protein |
| 19 | Nucleotide | Nucleotide sequence encoding 321th-537th amino acids of S protein |
| 20 | Nucleotide | Nucleotide sequence encoding 336th-516th amino acids of S protein |
| 21 | Peptide | Foldon domain |
| 22 | Nucleotide | Codon optimized nucleic acid sequence of SK-E-N |
| 23 | Peptide | GSGSG linker (SEQ ID NO: 23) |
| 24 | Peptide | GSSG linker (SEQ ID NO: 24) |
| 25 | Peptide | GSGGS linker (SEQ ID NO: 25) |
| 26 | Peptide | GSGS linker (SEQ ID NO: 26) |
| 27 | Peptide | GSGSSG linker (SEQ ID NO: 27) |
| 28 | Peptide | pelB leader sequence |

Advantageous Effects

The recombinant protein and/or recombinant virus vaccine according to one embodiment of the present invention has high safety.

The vaccine according to one embodiment of the present invention has excellent immunogenicity, and has excellent efficacy as a vaccine.

The vaccine of the present invention has a high neutralizing antibody titer.

The vaccine of the present invention has an excellent effect of induction of cellular immunity.

The present invention is excellent in prevention against SARS-coronavirus-2 infection.

The recombinant antigen protein of the present invention can maintain complete ACE2 binding function, and can maintain a three-dimensional RBD protein structure in a stable form. Using the recombinant antigen of the present invention, a high antibody production rate can be obtained.

The antigen protein of the present invention can exclude an undesired disulfide bond, and increase consistency of a disulfide bond pattern, so it is easy to control refolding of protein, and therefore, it can maintain complete ACE2 binding ability, and stably maintain a three-dimensional structure of protein.

BRIEF DESCRIPTION OF THE DRAWINGS

The following drawings attached in the present description illustrate preferable examples of the present invention, and play a role of further understanding the technical spirit of the present invention with the aforementioned contents of the invention, so the present invention should not be construed as limited only to matters described in such drawings.

FIG. 1 shows a schematic diagram of the SARS-COV2 spike full-length protein domain structure.

FIG. 2 is a drawing which illustratively shows a construct for expressing the recombinant antigen protein according to one example of the present invention. Regarding the numbers mentioned in the drawing of FIG. 2, for example, the expression construct referred to as SK-E-RBD-P2 means having a nucleotide expressing amino acids corresponding to the 336th position to 516th position of the S protein of SARS-coronavirus-2.

MODE FOR INVENTION

Figure 3:
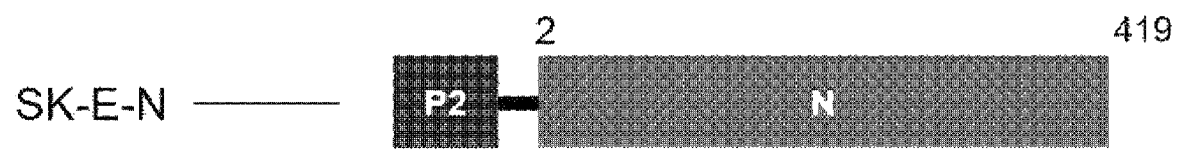
FIG. 3 is a drawing which schematizes the expression construct expressing a recombinant nucleocapsid (N) protein comprised as an adjuvant which can be comprised in the vaccine composition of the present invention.

Hereinafter, in order to help understanding of the present invention, it will be described in detail by examples and the like. However, the examples according to the present invention may be modified into various other forms, and it should not be construed that the scope of the present invention is limited by the following examples. The examples of the present invention are provided to describe the present invention more completely to those skilled in the art to which the present invention belongs.

1. Preparation of Antigen Using Spike Protein of SARS-Coronavirus-2

In order to construct an antigen protein used for vaccine preparation, referring to the sequence of Genbank #MN908947 Severe acute respiratory syndrome coronavirus 2 isolate Wuhan-Hu-1, S gene and N gene sequences were prepared.

Figures 1, 2:
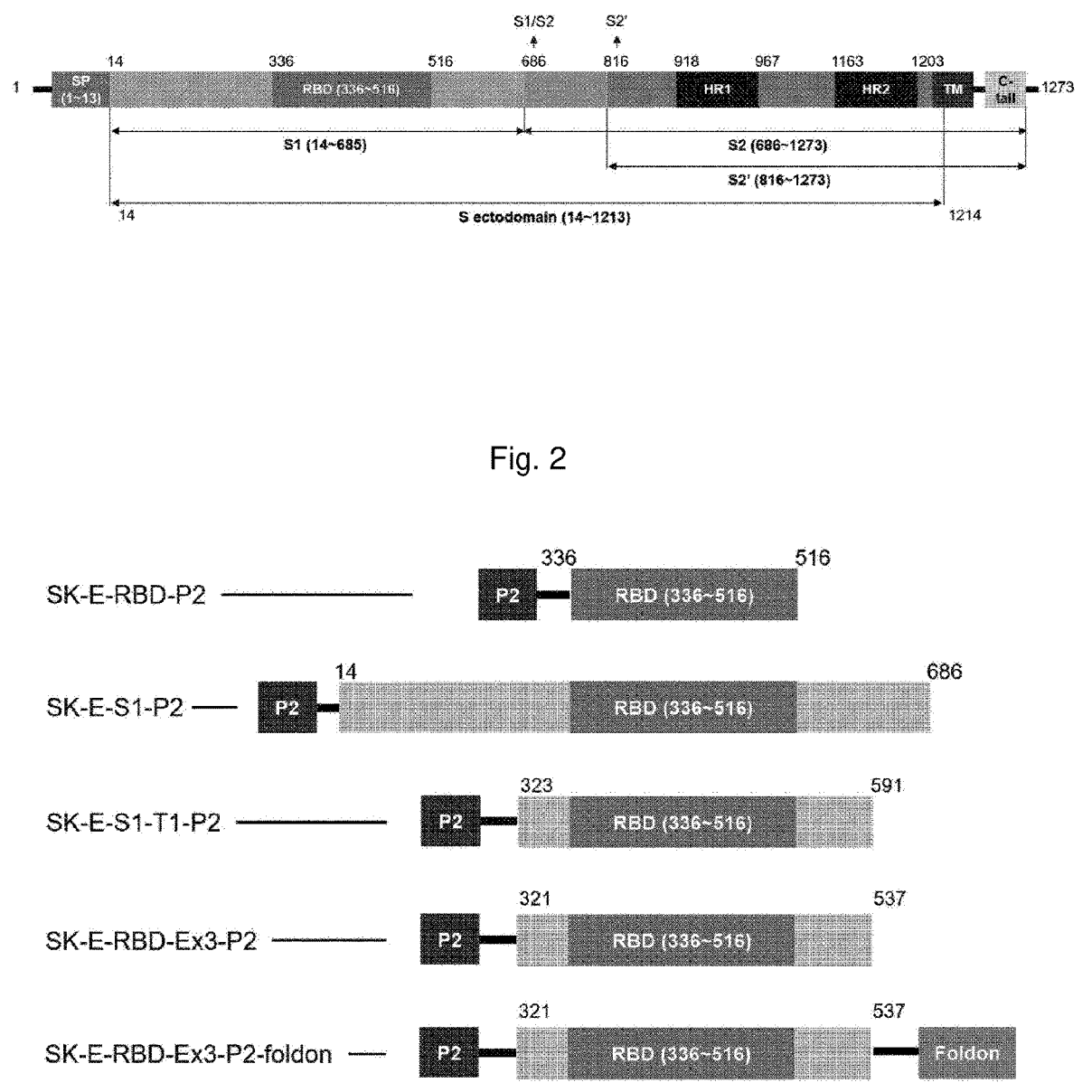

FIG. 1 shows a schematic diagram of the SARS-COV2 spike full-length protein domain structure. The recombinant antigen protein was prepared using the S1 subunit of the SARS-COV2 spike consisting of amino acids from position 14th to position 686th.

For expression of the SARS-coronavirus-2 antigen protein, various series of expression constructs were designed. The expression constructs were illustrated in detail in FIG. 2. P2 means a Tetanus P2 domain (CD4 T cell epitope). Herein, the P2 domain was linked by a GSGSG peptide linker (SEQ ID NO: 23), and the foldon was linked by a GSGGS linker (SEQ ID NO: 25).

In addition, a recombinant antigen protein in which the T cell epitope P2 domain was linked by a GSGSG peptide linker (SEQ ID NO: 23) to the RBD and the extended RBD was constructed.

It could be seen that the designed recombinant antigen protein had an excellent protein expression rate, and had excellent refolding efficiency.

2. Preparation of Antigen Using Other Protein

Based on the N protein gene of SARS-corona-2 virus, an N protein antigen of SEQ ID NO: 16 was prepared.

3. Codon Optimization

DNA sequences encoding recombinant proteins were synthesized with codons optimized for *E. coli* in GenScript. They were represented by SEQ ID NOs: 11 to 15.

4. Preparation of Recombinant Protein Vaccine

A process of producing recombinant protein using an *E. coli* expression system is as follows.

(1) In order to express an antigen protein having any one amino acid sequence of SEQ ID NOs: 6 to 10, each gene was synthesized by *E. coli* codon optimization. The synthesized genes were inserted into an expression vector and cloned, and the gene sequences were analyzed.

(2) A recombinant plasmid was transformed into an *E. coli* cell for producing protein.

(3) Using an antibiotic, a transformed cell expressing recombinant protein was identified.

(4) The identified transformed *E. coli* cell was mass-cultured, and the recombinant protein was overexpressed through IPTG induction.

(5) Recombinant protein purification

Mass-cultured cells were collected and dissolved, and then an inclusion body of the antigen protein was secured, and then a re-folding process was performed, and the refolded protein was purified using an appropriate chromatography method (Ion Exchange, Size Exclusion, etc.).

(6) Recombinant protein confirmation and quantification

Expression and purity of the recombinant protein were confirmed using SDS-PAGE and Western blot methods. The recombinant protein was quantified using a total protein quantification method (Lowry method, BCA method, etc.).

5. Evaluation of Recombinant Antigen Protein

A. Animal Experiment 1.2.1 Immunogenicity Test 1.2.1.1 The purified recombinant protein was inoculated into an animal model in combination with an adjuvant (e.g., Aluminum hydroxide) at an interval of 2~3 weeks 2~3 times.

1.2.1.2 Confirmation of safety by measuring change in body weight and body temperature 1.2.1.3 After 2~3 weeks of final inoculation, serum and splenocytes isolated from whole blood were obtained.

1.2.2 Protection Test 1.2.2.1 The purified recombinant protein was inoculated into an animal model in combination with an adjuvant (e.g./Aluminum hydroxide) at an interval of 2~3 weeks 2~3 times.

1.2.2.2 After 2~3 weeks of final inoculation, a lethal dose of wild-type SARS-coronavirus-2 virus was infected.

1.2.2.3 For 1 week after infection, virus shedding was evaluated in the liver, nasal cavity, respiratory tract, organ and the like.

1.2.2.4 For 2 weeks after infection, the body weight, change in the body weight and body temperature, death rate, and the like were evaluated.

B. Immunogenicity Evaluation 1.3.1 IgG ELISA 1.3.1.1 Antigens for coating (RBD, S1, S2, N, etc.) were coated in a 96-well plate, and the plate was blocked with a blocking buffer. A sample (serum) was reacted on the plate. An IgG detection antibody was reacted on the plate. By adding a substrate buffer to develop color, the absorbance was measured.

TABLE 2

| No. | Antigen | Antigen concentration (μg) | Number of subjects | Adjuvant | RBD-specific IgG-5w | N-specific IgG-5w |
|---|---|---|---|---|---|---|
| 1 | Vehicle | 0 | 5 | AddaVax | 25 | 221 |
| 2 | SK-E-RBD-P2 + N | 5 + 0.5 | 5 | AddaVax | 4,649 | 875,739 |
| 3 | SK-E-S1-T1-P2 | 10 | 5 | Alum. H | 22,046 | 94 |

TABLE 3

| No. | Antigen | Antigen concentration (μg) | Number of subjects | Adjuvant | RBD-specific IgG-6w | N-specific IgG-6w |
|---|---|---|---|---|---|---|
| 1 | Vehicle | 0 | 10 | Alum. H | 25 | 25 |
| 2 | SK-E-RBD-P2 | 10 | 10 | Alum. H | 376,491 | 25 |
| 3 | SK-E-RBD-P2 + N | 10 + 10 | 10 | Alum. H | 39,127 | 256,683 |
| 4 | SK-E-RBD-P2 | 20 | 10 | Alum. H | 633,722 | 25 |
| 5 | SK-E-RBD-P2 + N | 20 + 20 | 10 | Alum. H | 59,767 | 265,289 |

1.3.2 Pseudovirus Preparation
   1.3.2.1 An S protein gene of SARS-coronavirus-2 was cloned into a vector for expression. A reporter gene was cloned into a transfer vector. Two genes were transformed into a cell for producing a pseudovirus to prepare a pseudovirus expressing a reporter protein.

1.3.3 Neutralizing Antibody Titer Evaluation 1.3.3.1 A serial-diluted sample (serum) was reacted with the pseudovirus. The reacted pseudovirus was infected into a cell for infection cultured in a 96 well-plate (Vero E6, etc.) and cultured. After 4~6 hours, it was washed with PBS and replated with a new medium. By culturing for 24~72 hours and comparing an expressed amount of the reporter protein, a neutralizing antibody titer was evaluated.

1.3.4 Cellular Immunity Evaluation 1.3.4.1 An anti-interferon-gamma antibody (anti-IFN-γ antibody) was coated on a 96 well-plate. The plate was blocked with a blocking buffer, and splenocytes and an accelerator antigen (stimulate) were added and cultured for 24~36 hours. An interferon-gamma detection antibody was reacted, and it was reacted by adding a substrate. Immunocytes were evaluated using ELISPOT reader.

1.3.4.2 For immune property analysis, an immunocyte-specific antibody and a cytokine antibody were reacted with the isolated splenocytes for 2 hours. Through flow cytometry, the T cell distribution and cytokine expression rate were measured.

C. Evaluation of Antigenicity of Antigen for Vaccine (CR3022 Binding Affinity Evaluation)

In order to evaluate the binding affinity to CR3022, BioLayer Interferometry (BLI) was used. CR3022 is a human monoclonal antibody against Recombinant SARS-CoV-2 Spike Glycoprotein S1. (CAT #: ab273073 of Abcam company)

BLI measures an affinity constant KD value (Kdis/Kon) through association and dissociation between an antibody and an antigen, and the smaller the value, the higher the affinity. A corona 19 S-specific antibody was immobilized on ProA sensor chip (ForteBio) using Octet K2. By dipping the sensor chip in an antigen sample 2-fold diluted from 100 nM, the association was measured, and by dipping it in a well comprising only Kinetic buffer, the dissociation was measured. Using Octet Data Analysis software (11.0), data obtained by subtracting the reference from the resulting value was analyzed by fitting to a 1:1 binding model.

D. Evaluation of Antigenicity of Antigen for Vaccine (ACE2 Binding Affinity Evaluation)

In order to evaluate the binding affinity to an ACE2 receptor, BioLayer Interferometry (BLI) was used. ACE2 is a receptor protein binding to an RBD part in Recombinant SARS-COV-2 spike protein (CAT #: 10108-H02H of Sino company).

BLI measures an affinity constant KD value (Kdis/Kon) through association and dissociation between an antibody and an antigen, and the smaller the value, the higher the affinity. An ACE2 receptor protein was immobilized on ProA sensor chip (ForteBio) using Octet K2. By dipping the sensor chip in an antigen sample 2-fold diluted from 100 nM, the association was measured, and by dipping it in a well comprising only Kinetic buffer, the dissociation was measured. Using Octet Data Analysis software (11.0), data obtained by subtracting the reference from the resulting value was analyzed by fitting to a 1:1 binding model.

6. Relationship Between Structure and Immunogenicity of Recombinant Antigen Protein The recombinant protein of SEQ ID NO: 5 is an RBD in the most compact structure. It is easy to refold an inclusion body.

The recombinant protein of SEQ ID NO: 4 increases 15 aa at the N-terminus and 21 aa at the C-terminus than SEQ ID NO: 5, and 1) By comprising C525, a pair of C391, a free thiol of SEQ ID NO: 5, during refolding, C391 and C525 were allowed to form a disulfide bond, and formation of a complete disulfide bond was induced, and formation of a functional structure was increased.

2) The extended N-terminus and C-terminus formed an additional beta sheet and loop and interacted with each other, thereby stabilizing the RBD terminal structure, leading to an immunogenicity increase. However, the reason why the immunogenicity was increased is not interpreted as limited to this theory.

The recombinant protein of SEQ ID NO: 3 has increased 15 aa at the N-terminus and 75 aa at the C-terminus than SEQ ID NO: 5, so that a subdomain is added, and it stabilizes the RBD structure, and increases an antigen size, leading to an immunogenicity increase. However, the reason why the immunogenicity was increased is not interpreted as limited to this theory.

Through this, synthesized sequences and information, protein expression confirmation, protein isolation purification, and recombinant protein vaccine candidate substances could be secured.

The vaccine candidate substances secured through this can prevent corona infection by inducing sufficient antibodies and protective immunity.

INDUSTRIAL AVAILABILITY

The present invention can provide a vaccine composition which can prevent infection of SARS-coronavirus-2. The present invention can provide a safe vaccine composition.

What is claimed is:

1. A pharmaceutical composition for preventing SARS-coronavirus-2 infectious disease, comprising
   i. a recombinant antigen protein for preventing SARS-coronavirus-2 infectious disease, comprising a SARS-coronavirus-2 polypeptide consisting of the amino acid sequence of SEQ ID NO: 3 or 4, and a Tetanus toxoid epitope P2 polypeptide consisting of the amino acid sequence of SEQ ID NO: 1, wherein the polypeptides are linked, and
   ii. one or more immunological adjuvant selected from the group consisting of aluminum hydroxide, aluminum phosphate, and hydrated aluminum potassium sulfate.

2. The pharmaceutical composition for preventing SARS-coronavirus-2 infectious disease according to claim 1, wherein each polypeptide is linked by a linker.

3. The pharmaceutical composition for preventing SARS-coronavirus-2 infectious disease according to claim 2, wherein the linker is a peptide linker of GSGSG (SEQ ID NO: 23) or GSGGS (SEQ ID NO: 25).

4. The pharmaceutical composition for preventing SARS-coronavirus-2 infectious disease according to claim 1, wherein in the recombinant antigen protein comprises, the polypeptide consisting of the amino acid sequence of SEQ ID NO: 1, the polypeptide consisting of the amino acid sequence of SEQ ID NO: 3, and a foldon domain consisting of the amino acid sequence of SEQ ID NO: 21 are sequentially connected, and each of them is linked by a linker.

5. The pharmaceutical composition for preventing SARS-coronavirus-2 infectious disease according to claim 1, wherein the recombinant antigen protein consists of any one amino acid sequence selected from SEQ ID NOs: 7, 8 and 10.

6. The pharmaceutical composition for preventing SARS-coronavirus-2 infectious disease according to claim 4, wherein the recombinant antigen protein consists of any one amino acid sequence selected from SEQ ID NOs: 7, 8 and 10.

7. A gene encoding the recombinant antigen protein for preventing SARS-coronavirus-2 infectious disease according to claim 1.

8. A gene encoding the recombinant antigen protein for preventing SARS-coronavirus-2 infectious disease according to claim 4.

9. The gene according to claim 7, wherein the gene consists of any one base sequence selected from SEQ ID NOs: 12, 13 and 15, which are codon-optimized for expression in *E. coli*.

10. A recombinant vector comprising the gene of claim 7.

11. An *E. coli* cell for expressing a SARS-coronavirus-2 antigen protein into which the recombinant vector of claim 10 is introduced.

12. A method for production of the recombinant antigen protein for preventing SARS-coronavirus-2 infectious disease of claim 1, comprising culturing the recombinant *E. coli* cell of claim 11 and isolating the recombinant antigen protein.

13. The pharmaceutical composition for preventing SARS-coronavirus-2 infectious disease according to claim 1, wherein the composition further comprises a pharmaceutically acceptable carrier.

14. The pharmaceutical composition for preventing SARS-coronavirus-2 infectious disease according to claim 4, wherein the composition further comprises a pharmaceutically acceptable carrier.

15. The pharmaceutical composition for preventing SARS-coronavirus-2 infectious disease according to claim 13, wherein the composition further comprises a nucleocapsid (N) protein of SARS-coronavirus-2 of SEQ ID NO: 16.

* * * * *